US006607918B2

(12) United States Patent
LaGraff et al.

(10) Patent No.: US 6,607,918 B2
(45) Date of Patent: Aug. 19, 2003

(54) FLUORESCENT LABELING METHOD AND SUBSTRATE (75) Inventors: John Robert LaGraff, Niskayuna, NY (US); James Claude Carnahan, Niskayuna, NY (US); D Sangeeta, Symmes, OH (US); James Anthony Ruud, Delmar, NY (US)

(73) Assignee: General Electric Company, Nishayuna, NY (US)

(*) Notice: Subject to any disclaimer, the term of this patent is extended or adjusted under 35 U.S.C. 154(b) by 261 days.

(21) Appl. No.: 09/773,152

(22) Filed: Feb. 1, 2001

(65) Prior Publication Data

US 2002/0142473 A1 Oct. 3, 2002

(51) Int. Cl.[7] .............................................. G01N 33/20
(52) U.S. Cl. ................. 436/73; 436/2; 436/5; 436/79; 436/80; 436/81; 436/82; 436/83; 436/84; 436/166; 436/172
(58) Field of Search ...................... 436/2, 5, 73, 79–84, 436/166, 172, 183

(56) References Cited

U.S. PATENT DOCUMENTS

| 4,054,535 A | * | 10/1977 | Molina .................. 252/301.19 |
| 4,323,785 A | * | 4/1982 | McComb et al. ........ 250/461 R |
| 4,610,966 A | * | 9/1986 | Fuchs ............................. 436/2 |
| 4,651,010 A | * | 3/1987 | Javan ...................... 250/458.1 |
| 4,774,188 A | * | 9/1988 | Chandross ..................... 436/5 |
| 4,858,465 A | * | 8/1989 | Molina ........................ 73/104 |
| 5,356,756 A | * | 10/1994 | Cavicchi et al. ............. 430/315 |
| 5,685,917 A | | 11/1997 | Sangeeta |
| 5,773,141 A | | 6/1998 | Hasz et al. |
| 5,851,678 A | | 12/1998 | Hasz et al. |
| 5,914,189 A | | 6/1999 | Hasz et al. |
| 5,928,948 A | * | 7/1999 | Malchesky ..................... 436/2 |
| 5,938,855 A | | 8/1999 | Bowden, Jr. |
| 5,965,446 A | * | 10/1999 | Ishikawa ........................ 436/5 |
| 5,985,356 A | * | 11/1999 | Schultz et al. .................. 427/8 |

FOREIGN PATENT DOCUMENTS

JP 11-281577 * 10/1999

OTHER PUBLICATIONS

Missel, L. et al, Chemical Abstracts 1968, 69, abstract 12446n.*
White, H. S. et al, Analytical Chemistry 1979, 51, 236–239.*
Patterson, M. L. et al, Analytical Chemistry 1985, 57, 2751–2752.*
Fujii, T. et al, Journal of Photochemistry and Photobiology A 1991, 61, 365–372.*

* cited by examiner

Primary Examiner—Arlen Soderquist
(74) Attorney, Agent, or Firm—Noreen C. Johnson; Christian G. Cabou (57) ABSTRACT A fluorescent probe is applied to bind to a metal oxide on a substrate and the substrate is exposed to an ultraviolet light to identify the metal oxide. A chemical cleaning or stripping solution is selected by combinatorial high throughput screening (CHTS). In the method, an array of regions is defined on a substrate, a candidate cleaning/stripping solution is deposited onto the regions to effect cleaning/stripping of the regions; a fluorescent probe is applied to bind to a metal oxide on the substrate; the substrate is exposed to an ultraviolet light to identify the metal oxide and a product of the cleaning/stripping is evaluated according to the identified metal oxide. An activated metal substrate composition is provided that comprises a metal substrate with a contaminant metal oxide coating and a fluorescent activator bound to the substrate by reaction with the metal oxide coating.

22 Claims, 5 Drawing Sheets

FLUORESCENT LABELING METHOD AND SUBSTRATE

BACKGROUND OF THE INVENTION

The present invention relates to a method for labeling metal oxides and to a labeled substrate. More particularly, the invention relates to a method for labeling deposits on turbine engine parts to determine effectiveness of cleaning/stripping solutions and procedures.

A typical gas turbine engine includes a compressor, a combustor and a turbine. Gases flow axially through the engine. Compressed gases emerging from the compressor are mixed with fuel and burned in the combustor. Hot products of combustion emerge from the combustor at high pressure and enter the turbine where thrust is produced to turn the turbine, which in turn drives the compressor.

The compressor and the turbine include alternating rows of rotating and stationary coated airfoils. High temperature combustion gases degrade the coatings through either hot corrosion or oxidation. Gases that circulate through the airfoils, particularly during operation on the ground, also include contaminants such as dirt that has been ingested by the engine. Accumulation of dirt can impede effective cooling and if melted, can infiltrate and destroy thermal barrier coatings (TBCs).

The dirt typically comprises mixtures of Ca, Mg, Al, Si, Ni and Fe carbonates and oxides such as multi-elemental spinels ($AB_2O_4$). The dirt oxides combine to form particularly deleterious calcium-magnesium-aluminum-silicon-oxide systems (Ca—Mg—Al—Si—O), referred to as CMAS. These contaminants can be in a molten state and can infiltrate pores and openings in engine parts to cause crack formation and part failure. Also, a low melting point eutectic $Ca_3Mg_4Al_2Si_9O_{30}$, similar in composition to diopside, can form from silicate-containing dirts at engine temperatures near 1200° C. The eutectic can wet and infiltrate coatings. Other contaminants include iron and nickel oxides, sodium vanadates, sodium sulfates, sodium phosphates and the like.

Other turbine engine part contaminants include thermally grown oxides (TGOs). High temperature engine operation can result in TGOs on coatings, which can unintentionally protect an underlying metal coating during chemical cleaning/stripping. For example, alumina scales that form on a diffusion, aluminide coating or on a metallic MCrAlY coating impede chemical attack during stripping, thus leading to incomplete coating removal or excessive base metal attack, both of which can lead to additional rework or part destruction. TGO systems include $Cr_2O_3$ and $Co_xCr_yO$ spinels, which form on cobalt-based superalloys such as FSX414. These systems can impede subsequent weld and braze repair processes.

Consequently, airfoils and other turbine engine parts are periodically cleaned and repaired by stripping degraded coatings, mechanically repairing the part and recoating the part substrate. Removal of the degraded coating can be accomplished through one or more stripping or cleaning immersions. Repair of turbine engine parts can also involve cleaning cracks, crevices and substrates to remove CMAS and other oxides, organic and inorganic impurities and dirt prior to alloy filling and brazing. A typical repair process consists sequentially of a dirt clean, coating strip, then a fluoride ion cleaning (FIC) or etching prior to weld/braze repair.

In another repair method, engine-run TBC coatings are stripped from aircraft blades by a caustic autoclave process. Chemical attack occurs at the interfacial alumina TGO, which develops between the bond-coat and the overlying TBC. However, the autoclave process often leaves residual alumina and TBC on the substrate. Residual alumina and TBC can impede subsequent re-coating repairs.

The effectiveness of a chemical cleaning/stripping system can be evaluated by an oxide detection procedure. This procedure involves a non-destructive (NDE) point probe technique using a surface capacitance probe, a surface resistance probe or a thermoelectric probe. However, these procedures are unreliable. The procedures detect gross regions of TGO but not small residual regions. Additionally, there is no NDE method to determine residual alumina or TBC after a TBC removal procedure.

There is a need for a reliable method to determine effectiveness of a cleaning/or stripping or TBC removal procedure. There is a need for a quick method to detect residual alumina and TBC material after caustic autoclave stripping of TBC to reduce rework.

BRIEF SUMMARY OF THE INVENTION

The invention relates to a method to determine effectiveness of a cleaning/stripping system. The invention provides a quick method to detect residual metal oxides including alumina and TBC material. According to the method, a fluorescent probe is applied to bind to a metal oxide on a substrate and the substrate is exposed to an ultraviolet light to identify the metal oxide.

In an embodiment, a chemical cleaning/stripping solution is selected by combinatorial high throughput screening (CHTS). In the method, an array of regions is defined on a substrate, a candidate cleaning/stripping solution is deposited onto the regions to effect cleaning/stripping of the regions; a fluorescent probe is applied to a residual metal oxide left on the substrate after the cleaning/stripping; the substrate is exposed to an ultraviolet light to identify the metal oxide and a product of the cleaning/stripping is evaluated according to the identified metal oxide.

In another embodiment, an activated metal substrate composition is provided that comprises a metal substrate with a contaminant metal oxide coating and a fluorescent activator bound to the substrate by reaction with the metal oxide coating.

DETAILED DESCRIPTION OF THE INVENTION

The invention relates to a method for selectively labeling surface oxide with a fluorescent probe. When exposed to ultraviolet light, the labeled regions luminesce to reveal residual oxide. For example, the oxide can be reacted with 3-aminopropyltriethoxysilane (GAP), which is then activated with fluorescamine. The method can be used to fluorescently label metal oxides such as CMAS, alumina and YSZ and to fluorescently label TGOs and TBCs. Some of the uses for the method include; (1) revealing residual TGOs on top of MCrAlY coatings, (2) revealing residual TGOs within engine part internal passageways, (3) revealing residual alumina on airfoils where a TBC has been stripped by a caustic autoclave process, (4) revealing residual TBC in cooling holes after an autoclave process, (5) automatically inspecting a coated part in combination with a camera and computer and (6) revealing any type of surface oxide on a metal surface.

In an embodiment, fluorescent labeling of the invention is incorporated into a combinatorial high throughput screening (CHTS) method to select a best case cleaning/stripping solution or condition. A CHTS method is characterized by parallel reactions on a micro scale. In one aspect, CHTS is described as a method comprising (A) an iteration of steps of (i) selecting a set of reactants or conditions; (ii) reacting the set and (iii) evaluating a product of the reacting step and (B) repeating the iteration of steps (i), (ii) and (iii) wherein a successive set of reactants or conditions selected for a step (i) is chosen as a result of an evaluating step (iii) of a preceding iteration.

The CHTS method can comprise steps of preparing a metal test substrate, assembling a mask onto the substrate to define an array of regions on the substrate, depositing a candidate cleaning/stripping solution onto the regions in a pattern defined by the mask to effect cleaning/stripping of the regions, applying a fluorescent probe to bind to oxides on the substrate, exposing the substrate to an ultraviolet light to identify metal oxides on the substrate and evaluating the cleaning/stripping solution according to the identified metal oxides. The regions can represent a combinatorial library of candidate cleaning/stripping solutions. The method can select a best solution from among a plurality of candidate cleaning/stripping solutions and/or the method can select a best set of conditions for cleaning/stripping solutions.

These and other features will become apparent from the drawings and following detailed discussion, which by way of example without limitation describe preferred embodiments of the present invention. In the drawings, corresponding reference characters indicate corresponding parts throughout the several figures. The exemplification set out herein illustrates a preferred embodiment of the invention, and such exemplification is not to be construed as limiting the scope of the invention.

Figure 1:
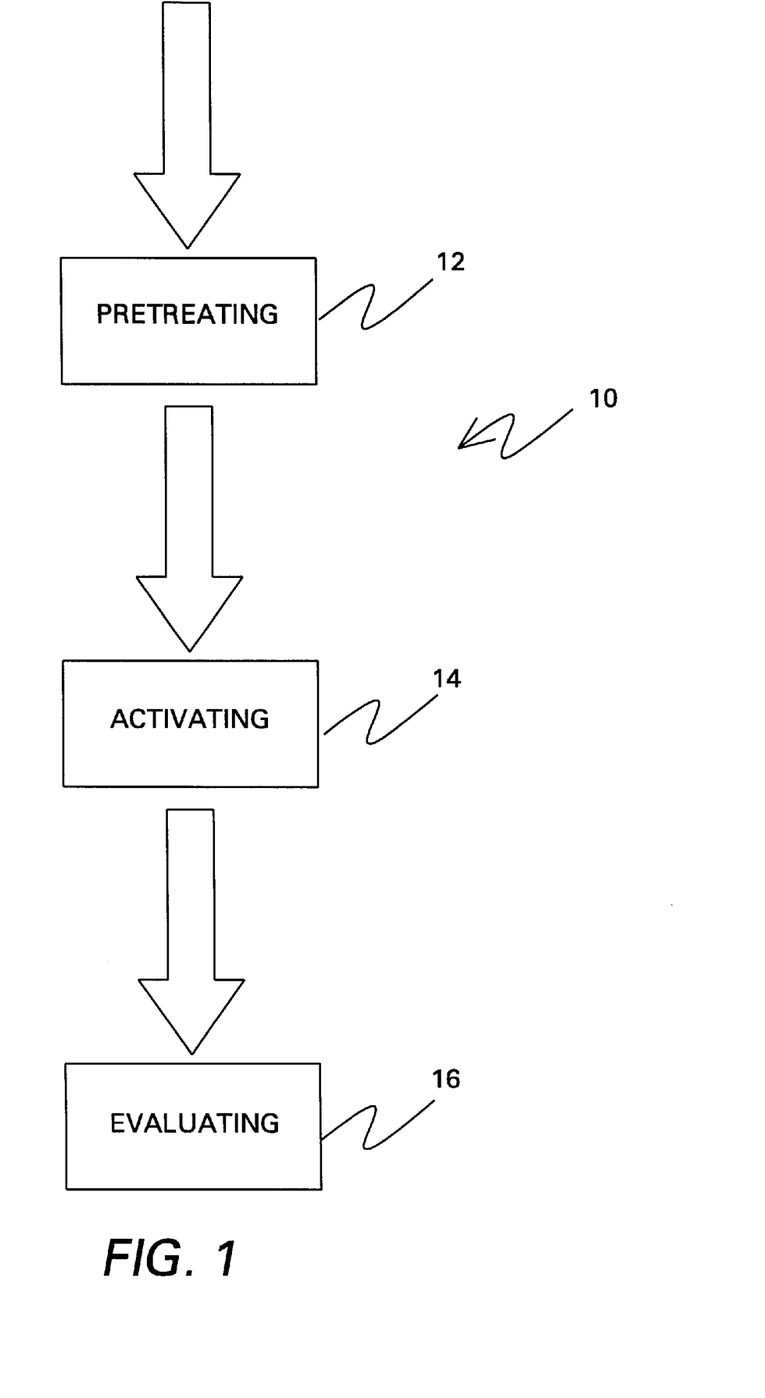
FIG. 1 is a flow diagram of a method for determining substrate cleanliness.

FIG. 1 illustrates a method of determining substrate cleanliness. The method 10 includes steps of pretreating 12 a substrate, activating 14 oxides on the substrate and detecting 16 the activated oxides. The oxides can be activated by applying an activator that reacts with the surface oxides and then reacting the activator with a probe to bind the probe to oxide areas as exemplified in FIG. 2.

Figure 2:
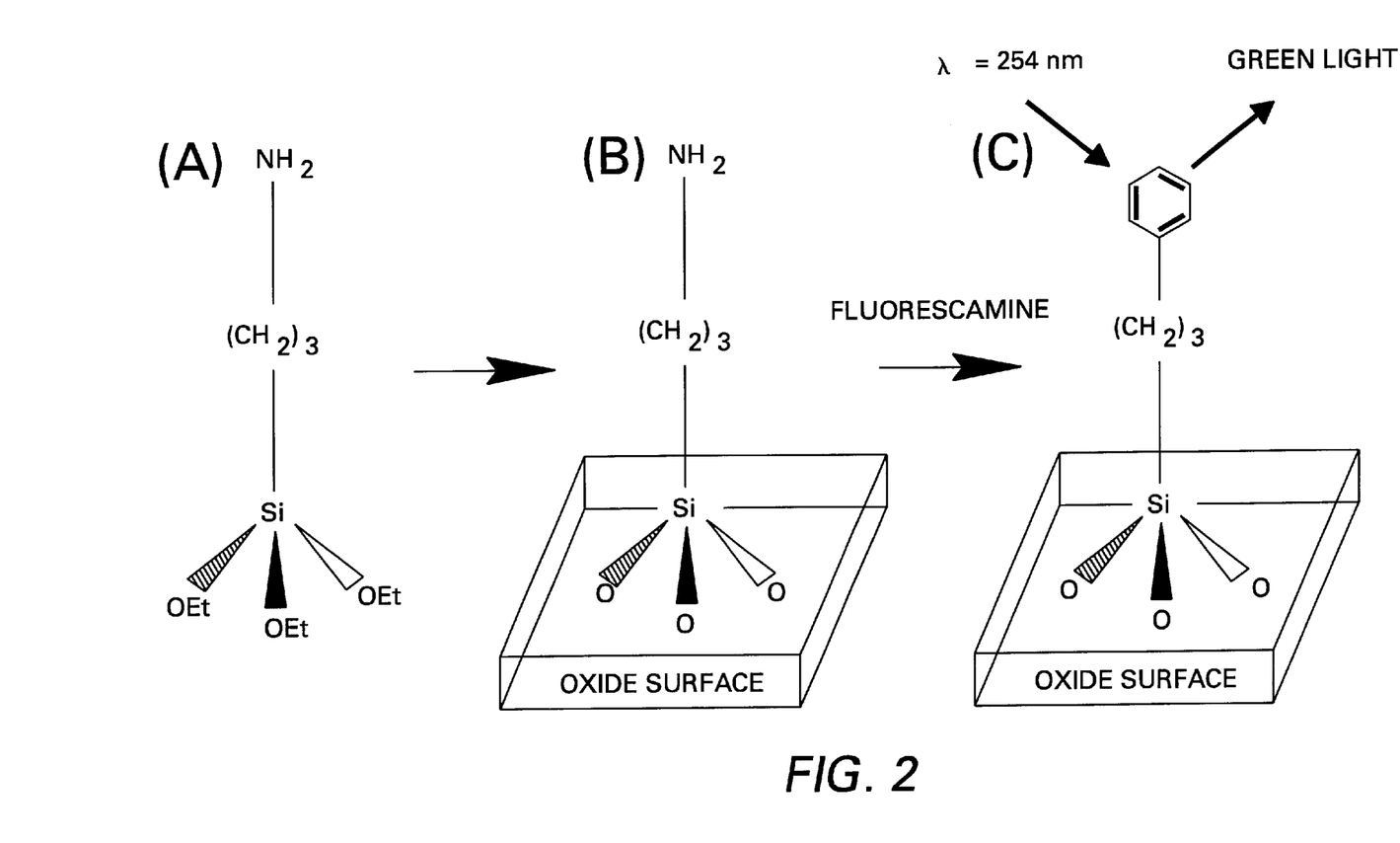
FIG. 2 is a schematic representation of an exemplary activating step of the invention.

Further with reference to FIG. 1, in the pretreating 12, first a substrate to be tested can be rinsed with a solvent or aqueous detergent to remove adhering oil and grease. For example, the substrate can be treated in a vapor or liquid degreasing bath. A vapor bath is preferred to reduce potential for redeposition of solubilized oil or grease. The substrate can also be treated with an acid or base wash to ensure that adhering dirt oxides are in an active form with a maximum level of surface hydroxyl groups for reaction as illustrated in FIG. 2.

The acid can be a mineral or organic acid chosen to avoid corrosion of the substrate. Suitable acids include a mineral acid selected from hydrofluoric, hydrochloric, hydrobromic, hydroiodic, sulfuric, sulfurous, phosphoric, nitric and perchloric acids. The acid can be concentrated or diluted with water to optimize pretreatment. An organic acid is also suitable. The organic acid can be selected from a carboxylic acid such as formic, acetic and acids with increasing carbon chain length. A suitable dicarboxylic acid can be selected from oxalic, maleic and subsequent members of the homologous series. Sulfonic acids such as methane sulfonic acid, trifluoric methane sulfonic acid and other halosulfonic acids are suitable. Suitable aromatic acids include benzoic and phthalic acids and substituted benzoic and phthalic acids.

The pretreatment 12 can be a treatment with a base such as an inorganic base or organic base. A suitable base can be selected from an alkali metal hydroxide, a carbonate, a bicarbonate ammonium hydroxide and ammonia. A suitable organic base can be selected from an an alkylammonium hydroxide, alkyl amine, alkyl polyamine, alkali metal alkoxide of a common alcohol and an alkali metal salt of ammonia.

The pretreatment 12 can be carried out at ambient temperature or at an elevated temperature to enhance treatment rate. The pretreatment chemicals can be removed with water or solvent wash before activation 14.

Activation 14 includes the application of an activator that bonds to the surface of the contaminant oxide on the metal but does not bond to the metal itself. The activator provides a fluorescent tag that is resistant to quenching and that is photo-stable to resist bleaching and thermally stable to resist deactivation during processing and measurement. The activator can provide an emission wavelength that is in the visible range and that is differentiated from any native fluorescence of the substrate. For example, some metal oxides have a faint blue-green fluorescence due to stress deformation. An activator for this application can be chosen to have a yellow or red fluorescence. In machine applications of this technique, narrow band-pass filters can be used to select specific emission wavelengths for optimum sensitivity and selectivity. Fluorescence lifetime gating of the detection device can be used to differentiate native fluorescence from longer lifetime phosphorescence.

The activator can be a combined reagent comprising a single molecule that includes both an oxide binding functionality and fluorescent functionality. The activator can be a multicomponent activator comprising a bifunctional reagent with a capability to react with the target contaminant oxide as well as a capability to react with a chosen fluorescent probe.

When the activator is a combined reagent, it can comprise a molecule that includes both an oxide binding functionality and fluorescent functionality. For example, N-triethoxysilylpropyl)dansylamide also known as 5-dimethylamino-N-(3-triethoxysilylpropyl)naphthalene-1-sulfonamide (CA registry #70880-05-6) can be applied as an activator by direct liquid application in a solvent such as toluene. N-triethoxypropylquinineurethan is another suitable activator. The activator can comprise an isocyanate, isothiocyanate, diazoalkane, boronate or sulfonyl halide substituted fluorescent probe. Suitable activators can be derived from amino, thio, hydroxyl and carboxyl reactive fluorescent probes listed in the Molecular Probes Catalog (Handbook of Molecular Probes and Research Chemicals, Sixth Ed. Richard P. Haugland, Molecular Probes, Eugene, Oreg. 97402). Other activators of this type can be synthesized from a reaction of another functionalized fluorescent probe with an appropriate reactive silane. Typical silane reactive substituents include amino, hydroxyl, carboxyl, silanol, thio and disulfide groups. A commercially available reactive silane can be prepared from 3-aminopropyltriethoxysilane and dansyl chloride.

The multicomponent activator includes a bifunctional reagent with a capability to react with the target contaminant oxide as well as a capability to react with a chosen fluorescent probe as illustrated in FIG. 2. A bifunctional reagent to react with the contaminant oxide can be selected from an alkoxy silane, silanol, silylamide, silane, acetoxysilane and silyl halide. Suitable activator reagents are available from Gelest Inc., (Tulleytown, Pa. 19007).

Exemplary alkoxy silanes include 3-aminopropy methoxy dimethylsilane, 3-aminopropyl dimethoxy, methylsilane and 3-aminopropyl trimethoxy silane. The alkoxy groups in a bifunctional reagent with a plurality of alkoxy groups can be of the same alcohol residue or of mixed alcohol residues. The alcohol can be selected from methyl, ethyl, propyl, isopropyl, butyl, isobutyl and tertiary butyl. Trialkoxy silanes are preferred due to the increased probability of multiple bonding with contaminant oxide. Aminoalkylsilanes are preferred because of their commercial availability and because of the large number of primary amine reactive fluorescent reagents.

Silyl halides can be chosen from fluoride, chloride, bromide or iodide. In the case of halide, the reactive functionality may be restricted due to potential reaction. For example, 3-aminopropyltrichlorosilane will exist as a cyclic aminosilane due to reaction of the Si—Cl with the amino functionality.

Dialkoxy silanes and alkoxysilanes are preferred bifunctional reagents. Trialkoxy silanes are most preferred bifunctional reagents. Silanes, silylamides and silanols may be preferred for special uses.

The bifunctional reagent can be applied to the test substrate neat with no added solvent, it can be applied in a non-reactive solvent and it can be applied with a reactive co-reagent. The co-reagent can be a substance to enhance hydrolysis, such as water or an alcohol. Suitable application methods include, immersing, spraying, brushing or rolling the bifunctional reagent onto the test substrate. The bifunctional reagent can be applied by immersing the test substrate into a vapor bath containing the neat reagent or it can be applied by immersing the test substrate into a vapor bath consisting of the reagent and an inert or possibly reactive co-reagent. The co-reagent can be a substance to enhance hydrolysis, such as water and/or alcohol.

The bifunctional reagent is then reacted with a suitable fluorescent probe. Suitable fluorescent probes include fluorescamine, ortho-phthaldialdehyde, naphthalene-2,3-dicarboxaldehyde and anthracene-2,3-dicarboxaldehyde. The probes can be sensitivity enhanced by mixing with bis-(2,4,6-trichlorophenyl)oxalate, which is a chemiluminescent agent.

In an exemplary application as shown in FIG. 2, a 1:1 mixture of 3-aminotriethoxysilane (A) and ethanol is applied to a test substrate with a brush. The mixture is allowed to remain for 15 minute at room temperature in ambient humidity and then excess reagent is rinsed off with ethanol liquid or by immersion in an ethanol vapor bath. The dried test material is then ready for attachment of the fluorescent probe via a free amino group. In another exemplary application, a mixed 3-aminotriethoxysilane (A) and argon is heated to generate a vapor bath. A substrate is immersed in the vapor. After several minutes exposure, the substrate is removed and unadsorbed activation reagent removed by washing with solvent or in a solvent vapor bath. The dried substrate is then ready for attachment of the fluorescent probe via a free amino group. After activating 14, the coating oxides can be detected 16 by irradiation with UV light. For example in FIG. 2, the bound 3-aminotriethoxysilane (B) is reacted with fluorescamine to provide a bound fluorescent probe (C) that emits a green light when irradiated at 254 nm.

Figure 3:
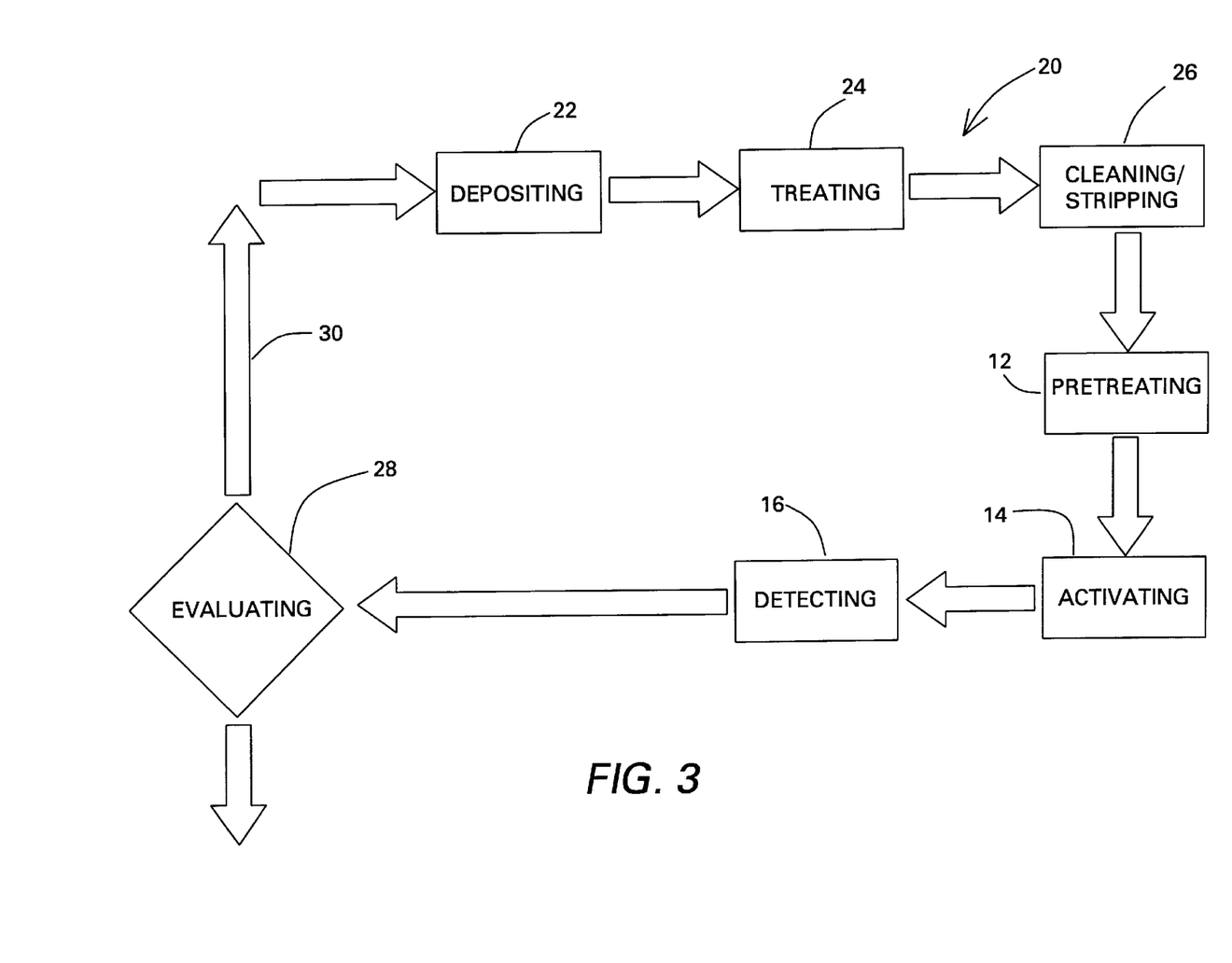
FIG. 3 is a flow diagram of a method for selecting a chemical cleaning/stripping solution.

In FIG. 3, a method 20 for selecting a chemical cleaning/stripping solution by CHTS includes steps of depositing 22 components of a contaminant library onto regions of a substrate to form at least two test contaminant members of the library, treating 24 the substrate with deposited contaminant by annealing or the like to simulate conditions of a used and dirtied engine part, cleaning or stripping 26 the substrate with a candidate cleaning/stripping solution and evaluating 28 cleanliness of the substrate to select a cleaning solution for at least one of the contaminant members. The evaluating 28 is based on detected residual coating oxides. The residual coating oxides can be detected after stripping/cleaning 26 by pretreating 12 the substrate, activating residual oxides 14 on the substrate and detecting 16 the activated residual oxides.

In one aspect shown in FIG. 3, a CHTS method 10 can be described as comprising steps of (i) depositing 22 components of a test contaminant library onto regions of a substrate to form at least two test contaminant members of the library; (ii) cleaning/stripping 26 the substrate with a candidate cleaning/stripping solution under a selected reaction condition; and (iii) evaluating a product of the cleaning/stripping step; and (B) reiterating 30 (A) wherein a successive solution or condition selected for a step (ii) is selected as a result of an evaluating step 28 (iii) of a preceding iteration of a step (A). A typical CHTS can utilize advanced automated, robotic, computerized and controlled loading, reacting and evaluating procedures.

The components of the test contaminant library can be deposited 22 by any suitable method. One method utilizes a multiple channel liquid dispensing system, wherein each of an array of liquid dispensers can be individually controlled and programmed to dispense a liquid material. In preferred embodiments, the liquid dispensers are each filled with a soluble metal precursor such as a nitrate, acetate or other aqueous soluble metal salt compound.

The test contaminant library is deposited on a substrate that can be a metal usually used in engine parts. The substrate can be a button or coupon of airfoil material or other engine part material or it can be a simple metal or alloy plate. Examples of substrates include NiAl, PtAl, McrAlY and yttrium-stabilized zirconia, chromides, etc. coated superalloys. Examples of superalloys include Ni-based superalloys in both equiaxed and single crystal form, such as Rene N5, GTD111, etc. and Co-based alloys such as FSX414. Also, the contaminant library can be placed on Pt foils to minimize reactions between contaminant and substrate during high temperature intermixing of deposited oxides.

In a preferred embodiment, a thin film contaminant library on a substrate is produced using a multiple gun sputtering deposition system. The multiple gun sputtering deposition system contains a contaminant component placed in each gun cavity. An electrical discharge can be created at each source by applying radio frequency (RF) or direct current (DC) power in a range between about 10 Watts and about 1,000 Watts through the sputter gun, which heats the contaminant component to form a metal plasma vapor. The metal vapor from the sputter gun is deposited onto a counter-facing substrate. The rate of the material deposition is dependent on the level of power input. The amount of material deposited can be altered by changing the amount of time the sputter gun is powered.

In various embodiments, the thin film contaminant oxide library is built with an in-vacuum feed-in system. This enables the contaminant oxide library to be made without breaking vacuum to change sources and masks for the next deposition, which keeps the metal contaminants in an atmospherically controlled environment. In particular, the in-vacuum feed-in system is filled with a gas, for example, argon, helium, nitrogen, hydrogen and mixtures thereof. The gas in the thin film contaminant library is referred to as "sputtering gas." The in-vacuum feed-in system increases the speed of generation of libraries and also prevents the formation of metal oxides from elemental metals and alloys that are sensitive to oxygen.

Figure 4:
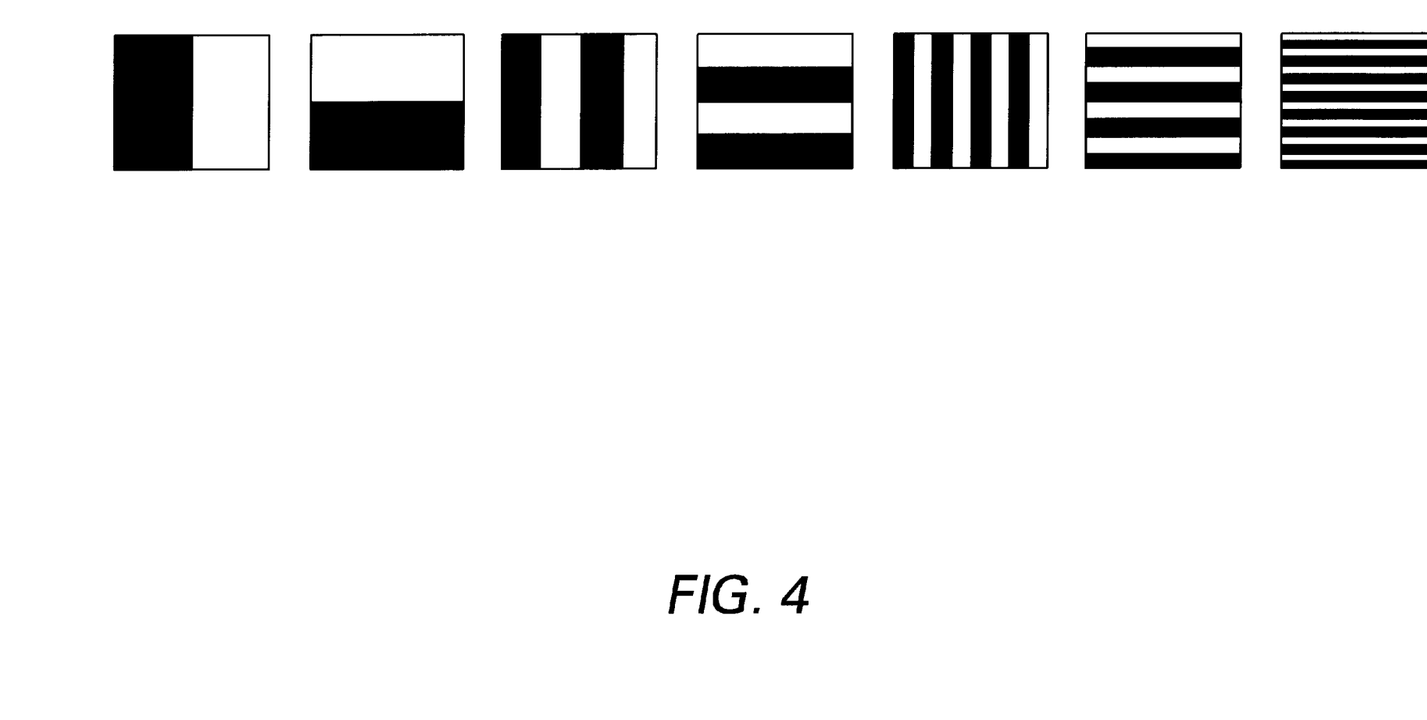
FIG. 4 is a schematic representation of a binary mask group.

Preferably, a binary masking strategy is used in making the contaminant library. FIG. 4 is an example of a suitable binary mask group that can provide a binary masking strategy to prepare a substrate supported contaminant library. The masks are all different. In the process, approximately one half of a mask area is covered during each elemental deposition step. The masking strategy includes choice of mask form as well as masking procedure. Examples of mask forms include a shadow mask, a lithographic mask and a movable-shutter mask. The first two masks can be used for a broad search of contaminant systems while a shutter mask can be used for composition optimization in a discovered system of cleaning solutions. In the deposition process, a primary mask is applied to spatially divide the substrate. Then a sequence of secondary masks can be overlaid. Controlled quantities of various contaminant library components can be deposited through the secondary masks. The sequence and pattern of the secondary masks determine final composition of contaminant materials in the library.

In binary masking strategy, one half of a total primary masking area can be covered on each elemental deposition step. The number of different contaminant library member compositions synthesized is $2^n$, where n is the number of operational steps. For example, 7 deposition steps represented by the 7 different masks of the group of FIG. 4, generate $128(2^7)$ different contaminant sample compositions on a substrate. Many possible combinations of the seven deposition entities can be created, from single elements, to binaries, ternaries, quaternaries, etc.

Referring again to FIG. 3, treating step 24 can be a furnace annealing, furnace cycling (i.e., repeated heating and cooling) or a burner rig test, which involves cyclic exposure to hot combustion gas impingement. Generally, the treating step 24 is carried out in an apparatus such as a furnace. In the furnace, the library is heated to a temperature in a range between about 200° C. and about 1100° C., and preferably, to a temperature in a range between about 600° C. and about 800° C. The heating can be in a non-organic gas environment to substantially prevent oxidation of elemental metals or metal alloys. Examples of typical gas environments include argon, helium, nitrogen, hydrogen and mixtures thereof.

Referring again to FIG. 3, a solution can be used to clean or strip 26 the library of contaminants to determine effectiveness of the solution for cleaning/stripping the wide variety of contaminants represented in the contaminant array. Extent and effectiveness of cleaning/stripping can then be detected 16 and evaluated 28.

The following Examples are illustrative and should not be construed as a limitation on the scope of the claims unless a limitation is specifically recited.

EXAMPLE 1

Residual oxides left after stripping a section of an airfoil with a caustic autoclave process were activated by reaction of GAP with surface hydroxide groups according to the procedure shown in FIG. 2. Fluorescamine was then used to activate the GAP modified oxides by reacting with the amine tail group ((C) of FIG. 2). Once activated, the oxides fluoresced when exposed to ultraviolet (UV) light.

Figure 5:
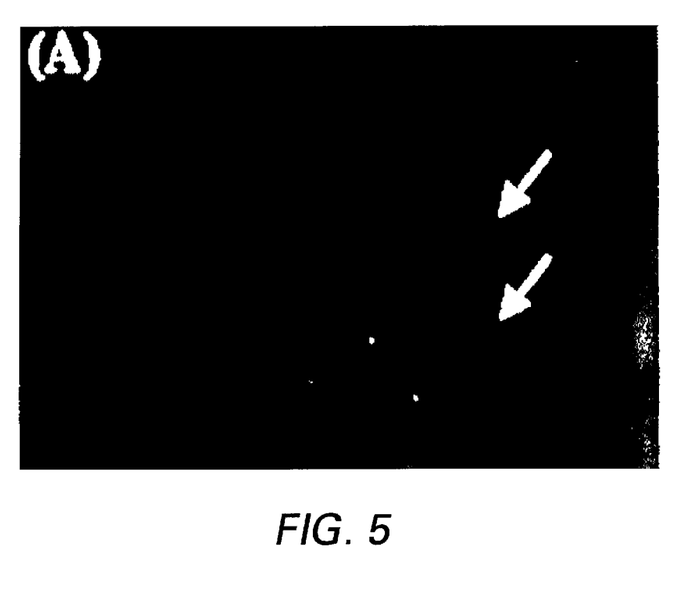
FIGS. 5 to 6 are photomicrographs of an oxide coated substrate.
Figure 6:
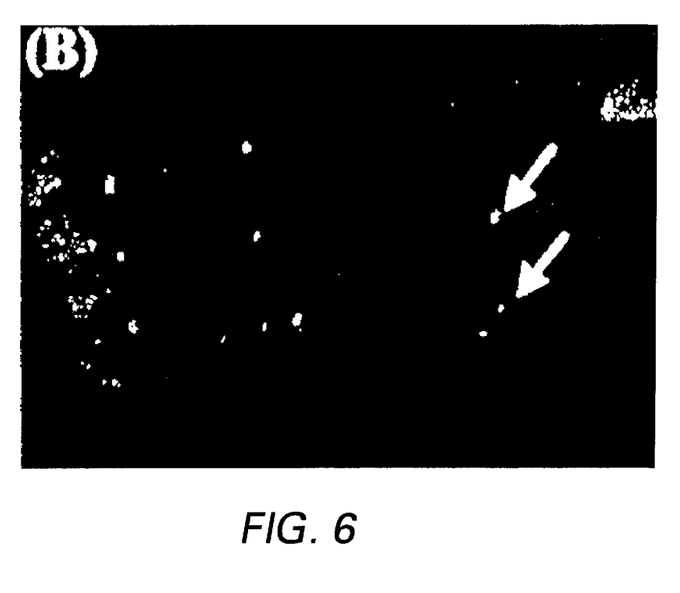

FIG. 5 shows a pressure side and FIG. 6 shows a suction side of a section of a stripped airfoil. The sides have an overall green glow under ultraviolet light due to fluorescent labeling of residual alumina particles. The arrows in FIGS. 5 and 6 are directed to cooling holes and point out GAP selectively labeled residual YSZ.

EXAMPLE 2

A combination of radio frequency (RF) sputtering and binary physical masking steps was used to generate a 128-member thin film dirt library, targeting various CMAS compositions. The sputtering solutions (>99.9% purity) included $CaCO_3$, $MgO$, $Al_2O_3$, and $SiO_2$. The libraries were deposited on silicon, flat steel, and Pt substrates. The amount of metals deposited was monitored in-situ with a quartz crystal thickness monitor. Analysis with a profilometer revealed that film thickness varied less than 5% over a two-inch diameter deposition area. Four identical libraries were fabricated and annealed in air from 800° C. to 1200° C. for 4 hours.

A compositional map of the libraries is shown in the TABLE.

TABLE

| | | | |
|---|---|---|---|
| caCa0.5Mg0.5Mg1.5AlAl0.5Si4.5 | caCa0.5Mg0.5AlAl0.5Si4.5 | caMg0.5Mg1.5AlAl0.5Si4.5 | caMg0.5AlAl0.5Si4.5 |
| caCa0.5Mg0.5Mg1.5AlAl0.5 | caCa0.5Mg0.5AlAl0.5 | caMg0.5Mg1.5AlAl0.5 | caMg0.5AlAl0.5 |
| caCa0.5Mg0.5Mg1.5AlSi4.5 | Ca0.5Mg0.5AlSi4.5 | Mg0.5Mg1.5AlSi4.5 | caMg0.5AlSi4.5 |
| caCa0.5Mg0.5Mg1.5Al | Ca0.5Mg0.5Al | Mg0.5Mg1.5Al | caMg0.5Al |
| caCa0.5Mg0.5Mg1.5Al0.5Si4.5 | Ca0.5Mg0.5Al0.5Si4.5 | Mg0.5Mg1.5Al0.5Si4.5 | caMg0.5Al0.5Si4.5 |
| caCa0.5Mg0.5Mg1.5Al0.5 | Ca0.5Mg0.5Al0.5 | Mg0.5Mg1.5Al0.5 | caMg0.5Al0.5 |
| caCa0.5Mg0.5Mg1.5Si4.5 | caCa0.5Mg0.5Si4.5 | caMg0.5Mg1.5Si4.5 | caMg0.5Si4.5 |
| caCa0.5Mg0.5Mg1.5 | caCa0.5Mg0.5 | caMg0.5Mg1.5 | caMg0.5 |
| caCa0.5Mg1.5AlAl0.5Si4.5 | caCa0.5AlAl0.5Si4.5 | caMg1.5AlAl0.5Si4.5 | caAlAl0.5Si4.5 |
| caCa0.5Mg1.5AlAl0.5 | caCa0.5AlAl0.5 | caMg1.5AlAl0.5 | caAlAl0.5 |
| caCa0.5Mg1.5AlSi4.5 | caCa0.5AlSi4.5 | caMg1.5AlSi4.5 | caAlSi4.5 |
| caCa0.5Mg1.5Al | caCa0.5Al | caMg1.5Al | caAl |
| caCa0.5Mg1.5Al0.5Si4.5 | caCa0.5Al0.5Si4.5 | caMg1.5Al0.5Si4.5 | caAl0.5Si4.5 |
| caCa0.5Mg1.5Al0.5 | caCa0.5Al0.5 | caMg1.5Al0.5 | caAl0.5 |
| caCa0.5Mg1.5Si4.5 | caCa0.5Si4.5 | caMg1.5Si4.5 | caSi4.5 |
| caCa0.5Mg1.5 | caCa0.5 | caMg1.5 | ca |

TABLE-continued

| | | | |
|---|---|---|---|
| Ca0.5Mg0.5Mg1.5AlAl0.5Si4.5 | Ca0.5Mg0.5AlAl0.5Si4.5 | Mg0.5Mg1.5AlAl0.5Si4.5 | Mg0.5AlAl0.5Si4.5 |
| Ca0.5Mg0.5Mg1.5AlAl0.5 | Ca0.5Mg0.5AlAl0.5 | Mg0.5Mg1.5AlAl0.5 | Mg0.5AlAl0.5 |
| Ca0.5Mg0.5Mg1.5AlSi4.5 | Ca0.5Mg0.5AlSi4.5 | Mg0.5Mg1.5AlSi4.5 | Mg0.5AlSi4.5 |
| Ca0.5Mg0.5Mg1.5Al | Ca0.5Mg0.5Al | Mg0.5Mg1.5Al | Mg0.5Al |
| Ca0.5Mg0.5Mg1.5Al0.5Si4.5 | Ca0.5Mg0.5Al0.5Si4.5 | Mg0.5Mg1.5Al0.5Si4.5 | Mg0.5Al0.5Si4.5 |
| Ca0.5Mg0.5Mg1.5Al0.5 | Ca0.5Mg0.5Al0.5 | Mg0.5Mg1.5Al0.5 | Mg0.5Al0.5 |
| Ca0.5Mg0.5Mg1.5Si4.5 | Ca0.5Mg0.5Si4.5 | Mg0.5Mg1.5Si4.5 | Mg0.5Si4.5 |
| Ca0.5Mg0.5Mg1.5 | Ca0.5Mg0.5 | Mg0.5Mg1.5 | Mg0.5 |
| Ca0.5Mg1.5AlAl0.5Si4.5 | Ca0.5AlAl0.5Si4.5 | Mg1.5AlAl0.5Si4.5 | AlAl0.5Si4.5 |
| Ca0.5Mg1.5AlAl0.5 | Ca0.5AlAl0.5 | Mg1.5AlAl0.5 | AlAl0.5 |
| Ca0.5Mg1.5AlSi4.5 | Ca0.5AlSi4.5 | Mg1.5AlSi4.5 | AlSi4.5 |
| Ca0.5Mg1.5Al | Ca0.5Al | Mg1.5Al | Al |
| Ca0.5Mg1.5Al0.5Si4.5 | Ca0.5Al0.5Si4.5 | Mg1.5Al0.5Si4.5 | Al0.5Si4.5 |
| Ca0.5Mg1.5Al0.5 | Ca0.5Al0.5 | Mg1.5Al0.5 | Al0.5 |
| Ca0.5Mg1.5Si4.5 | Ca0.5Si4.5 | Mg1.5Si4.5 | Si4.5 |
| Ca0.5Mg1.5 | Ca0.5 | Mg1.5 | |

EXAMPLE 3

Next, various fluorophores are screened for their ability to decorate deposits that are fired at different temperatures. GAP is dissolved in ethanol in several different ratios (e.g., 1–5 drops/ml). Each solution is spread on a substrate. After 5 minutes residence, the substrates are rinsed in ethanol. The resulting surface attached GAP is then reacted with fluorescamine, which is mixed in a ratio of 15 mg/ml. The substrates are allowed to dry and are then rinsed with acetone. UV light is irradiated on the substrates to determine which GAP/ethanol solution works best. Observation of the illumination determines that 5 drops/ml solutions label all oxides with the brightest signal.

EXAMPLE 4

Next, development time is determined. The GAP is removed from the substrates by rinsing in NaOH. Then 5 drop/ml GAP solutions are applied and the solutions on the substrates are developed for 5, 10, 20 and 30 minutes. The development conditions are repeated and the libraries are examined in UV light. The 20 minute development time shows a dramatic improvement in brightness. No further improvement is noted at 30 minutes.

The Examples show that metal oxide arrays can be provided and used to test for effectiveness of oxide cleaning or stripping. The Example also illustrate a determination of best conditions for testing for cleaning/stripping effectiveness.

What is claimed is:

1. A method to identify a metal oxide contaminant on a substrate, comprising:
    applying a fluorescent activator comprising a bifunctional reagent to bind to the metal oxide and reacting the bonded bifunctional reagent with a fluorescent probe wherein the fluorescent probe is mixed with a chemiluminescent agent; and
    exposing the substrate to an ultraviolet light to identify the metal oxide.

2. The method of claim 1, comprising pretreating the substrate.

3. The method of claim 2, wherein the pretreating comprises rinsing with a solvent or aqueous detergent to remove adhering oil and grease.

4. The method of claim 2, wherein the pretreating comprises treating in a vapor or liquid degreasing bath.

5. The method of claim 2, wherein the pretreating comprises treating with an acid or base wash.

6. The method of claim 5, wherein the acid is a mineral acid selected from the group consisting of hydrofluoric, hydrochloric, hydrobromic, hydroiodic, sulfuric, sulfurous, phosphoric, nitric and perchloric acids or organic acid selected from the group consisting of sulfonic acid, carboxylic acid and dicarboxylic acid.

7. The method of claim 6, wherein the carboxylic acid is selected from the group consisting of formic acid, acetic acid and subsequent members of a homologous series of acetic acid and the dicarboxylic acid is selected from the group consisting of oxalic, maleic and subsequent members of the homologous series of maleic acid.

8. The method of claim 5, wherein the acid is an aromatic acid selected from the group consisting of benzoic acid, phthalic acid, substituted benzoic acid and substituted phthalic acid.

9. The method of claim 5, wherein the base is an inorganic base selected from the group consisting of an alkali metal hydroxide, a carbonate, a bicarbonate, ammonium hydroxide and ammonia or the base is an organic base selected from the group consisting of an alkylammonium hydroxide alkyl amine, alkyl polyamine, alkali metal alkoxide of an alcohol and an alkali metal salt of ammonia.

10. The method of claim 1, wherein the activator bonds to the surface of a contaminant oxide on the substrate.

11. The method of claim 1, wherein the step of applying a fluorescent activator comprises applying a bifunctional reagent to bind with a metal oxide on the substrate and reacting the bonded bifunctional reagent with a fluorescent probe.

12. The method of claim 11, wherein the bifunctional reagent is applied without solvent or in a non-reactive solvent.

13. The method of claim 11, wherein the bifunctional reagent is applied with a reactive co-reagent to enhance hydrolysis of the metal oxide.

14. The method of claim 11, wherein the bifunctional reagent is applied by immersing, spraying, brushing or rolling the bifunctional reagent onto the substrate.

15. The method of claim 11, wherein the bifunctional reagent comprises at least one reactive group functionality selected from the group consisting of an alkoxy silane, silanol, silylamide, silane, acetoxysilane and silyl halide.

16. The method of claim 11, wherein the bifunctional reagent is an alkoxy silane selected from the group consisting of 3-aminopropy methoxy dimethylsilane, 3-aminopropyl dimethoxy,methylsilane and 3-aminopropyl trimethoxy silane.

17. The method of claim 11, wherein the bifunctional reagent comprises at least one trialkoxy silane reactive group functionality.

18. The method of claim 11, wherein the bifunctional reagent is an aminoalkylsilane.

19. The method of claim 11, wherein the bifunctional reagent comprises at least one silyl halide reactive group functionality.

20. The method of claim 11, wherein the bifunctional reagent is 3-aminopropyltrichlorosilane.

21. The method of claim 11, wherein the bifunctional reagent comprises at least one reactive group functionality selected from the group consisting of a silane, silylamide and silanol.

22. The method of claim 11, wherein the fluorescent probe is mixed with a chemiluminescent agent comprising bis-(2, 4,6-trichlorophenyl)oxalate.

* * * * *